United States Patent
Takeshita et al.

[11] Patent Number: 5,789,186
[45] Date of Patent: Aug. 4, 1998

[54] MARKER FOR CEREBRAL APOPLEXY

[75] Inventors: Hitoshi Takeshita, Shiga-ken; Hiroshi Morita, Osaka-fu; Akira Fujiwara, Osaka-fu; Yasutaka Kaneda, Osaka-fu; Tohru Watanabe, Osaka-fu; Taizou Hayashi, Osaka-fu; Kohji Uchida, Shiga-ken; Yushi Matsuo, Osaka-fu; Takekazu Horio, Osaka-fu, all of Japan

[73] Assignee: Oriental Yeast Co., Ltd., Tokyo, Japan

[21] Appl. No.: 656,934

[22] Filed: Jun. 3, 1996

[30] Foreign Application Priority Data

Jun. 1, 1995 [JP] Japan .................................... 7-156735

[51] Int. Cl.$^6$ .................... C12Q 1/34; C12Q 1/32; C12Q 1/42; C12Q 1/48
[52] U.S. Cl. ................. 435/18; 435/26; 435/4; 435/21; 435/15; 435/14; 435/183; 435/194; 436/63; 436/74; 562/587; 562/589
[58] Field of Search .................. 435/18, 26, 4, 435/21, 15, 14, 183, 194; 562/587, 589; 436/63, 74

[56] References Cited

FOREIGN PATENT DOCUMENTS 0292171  11/1988  European Pat. Off. .

OTHER PUBLICATIONS

Uchida et al, Japanese Jour of Clinical Chem, vol. 23, No. hosatsu2, p. 113b (1994) Month not available.
Batke, et al, Archives of Biochem and Biophysics, vol. 264, No. 2, Aug. 1, 1988, pp. 510–518.
Granstrom et al, "Inactivation of Type MM Phosphoglycerate Mutase by Sulfhydryl Group Reagents During Facial Embryogenesis", Acta Odontologica Scandinavica, 46:5 pp. 273–279, 1988.
Carreras et al, "Phylogeny and Ontogeny of the Phosphoglycerate Mutases—III. Inactivation of Rabbit Muscle Phosphoglycerate Mutase (Type M Isozyme) by the Sulfhydryl Group Reagents", Comparative Biochemistry and Physiology, 71:1, pp. 57–63, 1982.
Biological Physical Chemistry, Japanese Journal of Electrophoresis, 1995, vol. 39 No. 2, pp. 1–6.
Isozymes III Developmental Biology, Clement L. Markert, Academic Press 1975, pp. 1006 thru 1018.
619th Meeting Cambridge, S. Yates et al, Plasma phosphoglycerate mutase muscle (M) isoenzyme is stikingly raised in Duchenne muscular dystrophy vol. 14 pp. 1165 thru 1166.

*Primary Examiner*—Louise N. Leary
*Attorney, Agent, or Firm*—Browdy and Neimark

[57] ABSTRACT

A sample is treated with a phosphoglyceric acid mutase (PGAM) inhibitor (polythionic acid (salt) such as potassium tetrathionate) to inactivate the M-type isozyme activity and the B-type PGAM is quantified by determining PGAM isozymes by a rate assay. The B-type PGAM is a novel marker for cerebral apoplexy, and the diagnosis of cerebral apoplexy is enabled by assaying it.

17 Claims, 1 Drawing Sheet

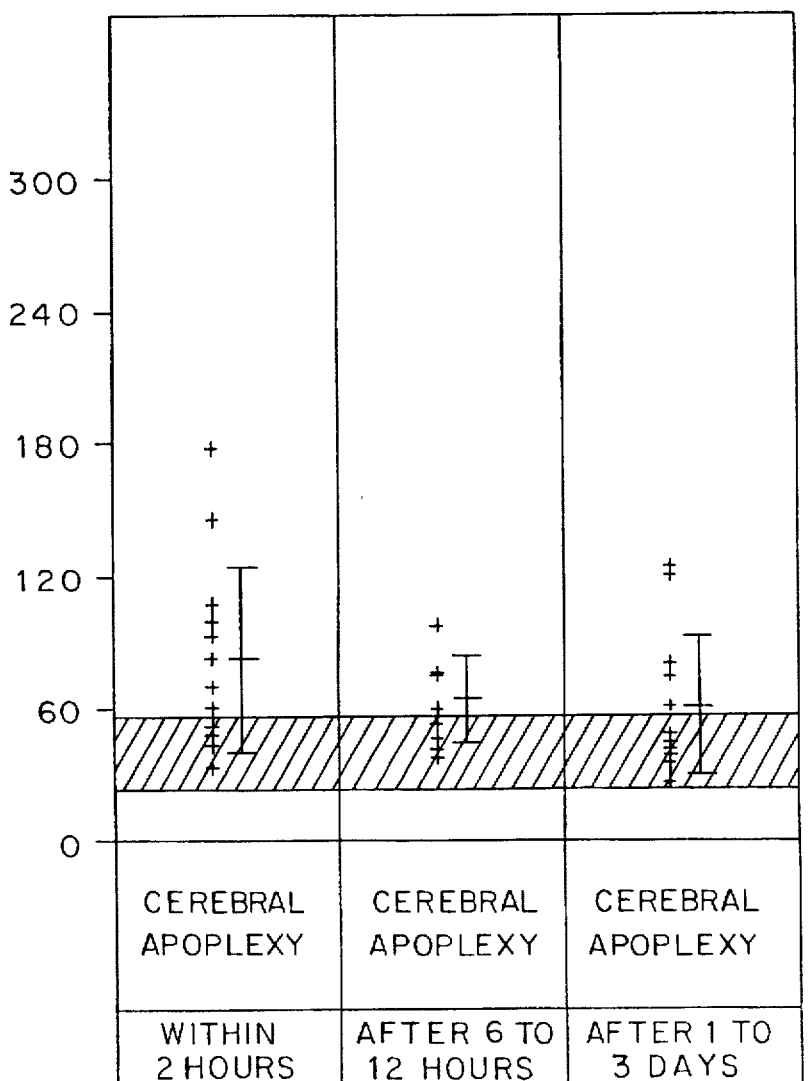

MARKER FOR CEREBRAL APOPLEXY

DETAILED DESCRIPTION OF THE INVENTION

1. Field of the Invention

The present invention relates to a novel system for assaying cerebral apoplexy.

2. Prior Art

Phosphoglyceric acid mutase (hereinafter sometimes referred to as PGAM; EC 5.4.2.1) is one of glycolytic enzymes and catalyzes reversible conversion between 2-phosphoglycerate (Glycerate-2-P) and 3-phosphoglycerate (Glycerate-3-P) in the presence of 2,3-bisphosphoglycerate (Glycerate-2,3-P2).

There are two genes each coding for PGAM in mammals. The gene of M subunit (molecular weight of about 30,000) is expressed in adult's skeletal muscle and heart muscle. In these tissues, there exists MM homodimer (hereinafter referred to as M-type PGAM, M-PGAM, PGAM-MM, PGAM-M or M-type isozyme). On the other hand, the gene of B subunit gene (molecular weight of about 30,000) is expressed in adult's brain, liver, kidney and erythrocytes, and BB homodimer (B-type PGAM, B-PGAM, PGAM-BB, PGAM-B or B-type isozyme) is found in these tissues. Accordingly, the M-type PGAM is classified into muscle-specific isozyme, while the B-type PGAM into non-muscle or brain isozyme. Both of M and B subunit genes are expressed specifically in heart muscle. In this tissue, there exists MB heterodimer (hereinafter referred to as MB-type PGAM, MB-PGAM, PGAM-MB or MB-type isozyme) in addition to the B-type and M-type PGAMS.

Yates et al proved, using isoelectric focusing which is capable of fractional determination of PGAM isozymes, that PGAM activity in normal plasma is mainly attributed to the B-type isozyme. Markert showed that the B-type isozyme of PGAM mainly exists in normal human fetus and adult's brain, whereas the MB-type and M-type isozymes are observed in cerebral tumor tissues, and their expression level is correlated with malignancy of tumor, although such a difference is not found in the case of creatine kinase (CK) which is one of the muscle-specific enzymes.

However, relationship between changes of PGAM isozymes in serum and various diseases has been hardly examined so far. Further, any marker for cerebral diseases are hardly known.

PROBLEMS TO BE SOLVED BY THE INVENTION

In any diseases, diagnosis at the early stage is indispensable. In particular, it has been strongly demanded to detect and accurately diagnose cerebral diseases such as cerebral apoplexy at the early stage.

BRIEF DESCRIPTION OF THE DRAWING

FIG. 1 shows time-course change of B-PGAM in a patient suffered from cerebral apoplexy after the onset of the disease.

MEANS FOR SOLVING THE PROBLEMS

The present invention was made in order to meet the requirements in this field of the art that a new system for rapid and accurate diagnosis of cerebral apoplexy should be urgently developed. More specifically, in view of the above-described technical background, the present invention was made in order to develop a simple and convenient method of assaying PGAM isozyme activity in serum, particularly the B-type isozyme which is specifically present in brain, and to make it clear that the PGAM isozyme is useful as a novel marker for cerebral apoplexy.

The present invention was made to achieve the above-described objects. As a result of extensive study from every point of view, it has been elucidated for the first time, using the following method, that the PGAM B-type isozyme is useful as a novel marker for cerebral apoplexy. Further, a method of directly assaying the B-type isozyme in a blood sample has been successfully developed to complete a total system for diagnosis and assay of cerebral apoplexy.

The present invention will be illustrated in detail below.

The assay method according to the present invention comprises treating a blood sample such as serum with a PGAM inhibitor to inactivate a specific isozyme, and then determining residual PGAM activity. For example, when tetrathionic acid is used as the PGAM inhibitor, almost 100% of M-type isozyme activity and about 50% of MB-type isozyme activity are lost, while B-type isozyme activity is hardly lost. Therefore, the B-type isozyme can be separately quantified by adding tetrathionic acid to serum to inactivate the M-type isozyme and measuring residual PGAM activity.

Incidently, according to the inhibition test using purified PGAM isozymes, only 50% of MB-type isozyme activity is lost by the treatment with tetrathionic acid, and 50% of the activity remains. However, since most of PGAM activities in normal serum and cerebral tissues are attributed to the B-type isozyme, residual activity of the MB-type isozyme can be practically disregarded in the case of diagnosis of cerebral apoplexy in a biological sample. Hence, an extremely simple, convenient, and practical assay has been enabled for the first time with the result of transcending mere theory.

Any substance capable of selectively inhibiting activity of PGAM or isozyme thereof, including an oxidizing agent, an SH reagent, can be used as the PGAM inhibitor. Non-limiting examples thereof include polythionic acid and/or derivatives thereof. As polythionic acid, any of tri- to hexathionic acid can be used. Examples of their derivatives include a potassium salt, a sodium salt and the like. One of suitable examples is potassium tetrathionate.

The assay method according to the present invention comprises allowing the inhibitor such as potassium tetrathionate to act on a blood sample such as serum so as to inactivate PGAM-M (PGAM-MB activity can be disregarded in this biological assay system as described above) and assaying residual PGAM-B using an assay reagent.

As shown in Table 1 below, the principle of the assay is based on the use of potassium tetrathionate as an M-type PGAM isozyme inhibitor to inactivate the M-type isozyme and the subsequent measurement of activity in the following manner. Namely, 3-phosphoglycerate (Glycerate-3-P) is converted into 2-phosphoglycerate (Glycerate-2-P) by PGAM-B in the presence of 2,3-bisphosphoglycerate (Glycerate-2,3-P2) and the resulting product is converted into PEP and $H_2O$ by enolase. Then, PEP is converted into pyruvate and ATP by pyruvate kinase (PK) in the presence of ADP, and lactate dehydrogenase (LDH) is acted on pyruvate thus obtained in the presence of NADH to conduct the rate assay of the decrease of NADH.

TABLE 1

Principle of Assay (1) Treatment with potassium tetrathionate
    PGAM-M: inactivated
(2) Activity assay $$\text{Glycerate-3-P} \xrightarrow[\text{Glycerate-2, 3-P2}]{\text{PGAM-B}} \text{Glycerate-2-P}$$

$$\text{Glycerate-2-P} \xrightarrow{\text{Enolase}} \text{PEP} + H_2O$$

$$\text{PEP} + \text{ADP} \xrightarrow{\text{PK}} \text{Pyruvate} + \text{ATP}$$

$$\text{Pyruvate} + \text{NADH} \xrightarrow{\text{LDH}} \text{Lactate} + \text{NAD}$$

The decrease of NADH can be easily measured using a commercially available measuring apparatus, thereby capable of an assay of PGAM-B accurately and rapidly. As is apparent from Examples shown below, the PGAM-B level in a serum sample derived from a patient with cerebral apoplexy is considerably high. In addition, high B-type isozyme activity is observed within such a short period of time as two hours after the occurrence of attack. Consequently, it has been found that the assay of PGAM-B is highly effective for diagnosis of cerebral apoplexy, and PGAM-B has been proved to be remarkably suitable as a marker for cerebral apoplexy. There has been no information so far that PGAM-B can be used as a marker for cerebral apoplexy. Hence, PGAM-B is regarded as a novel marker for cerebral apoplexy.

Further, according to the present invention, there is provided a reagent for assaying PGAM-B comprising enolase, pyruvate kinase (PK), NADH, lactate dehydrogenase (LDH), a PGAM inhibitor (potassium tetrathionate) and, if required, a substrate and a buffer. This can be used as a diagnostic agent for cerebral apoplexy. The reagent of the present invention can be marketed as a kit including Reagent 1 and Reagent 2 as exemplified in the following Examples.

In addition to the PGAM-B assay as described above, total PGAM (hereinafter sometimes simply referred to as PGAM or T-PGAM) shows the same behavior as the B-type isozyme, although it is somewhat inferior in accuracy to PGAM-B. In fact, it is observed in a serum sample derived from a patient with cerebral apoplexy at considerably high level, which is obtained within two hours after the occurrence of attack. Hence, T-PGAM is also highly useful as a novel marker for cerebral apoplexy.

The assay method of T-PGAM is completely same with the case of the B-type isozyme except that the inhibitor is not used (the principle of the assay is also quite same with that shown in Table 1 except the step (1) using the inhibitor and except using T-PGAM in place of PGAM-B in the step (2). Thus, the rate assay of the decrease of NADH can be carried out. As in the case of the B-type isozyme, the assay of T-PGAM can be also used for diagnosis of cerebral apoplexy. The accuracy of the T-PGAM assay is not so high as that of the B-type isozyme assay, but it does not require the inhibitor. Therefore, this method is also highly effective for diagnosis of cerebral apoplexy.

The reagent and the kit for the T-PGAM assay are completely same with those for the B-type isozyme assay except that the inhibitor is not used. For the same reason as described above, these can be used highly effectively as a diagnostic agent for cerebral apoplexy.

The present invention will be described with reference to the following Examples.

EXAMPLE 1

Effect of potassium tetrathionate on PGAM-B and PGAM-M was examined by an automatic assay method.

Standard preparations of the B-type and M-type isozymes (pooled serum base) were used as samples. These were diluted 1/1 to 1/8 with physiological saline to serve as samples. To the thus prepared samples were added potassium tetrathionate of various concentrations. After the reaction was carried out for 5 minutes, the quantity of the B-type and M-type PGAMs were determined by the automatic assay method.

The quantity of PGAM-B and PGAM-M were respectively determined using the reagent of Example 2 by the automatic assay method, and the results shown in Table 2 below were obtained. As is clear from the results, it has been found that the M-type isozyme was specifically inactivated by potassium tetrathionate, while no effect was observed in the B-type isozyme.

TABLE 2

Effect of potassium tetrathionate on PGAM-B and -M

|  | Dilution rate | \multicolumn{4}{c}{Final concentration of potassium tetrathionate (mM)} | | | |
|---|---|---|---|---|---|
|  |  | 0 | | 1.9 | 3.8 | 7.6 |
| PGAM-B | 1/8 | 100 | (22 U/L) | 93 | 93 | 75 |
| standard | 1/4 | 100 | (46 U/L) | 97 | 86 | 59 |
| (pooled serum | 1/2 | 100 | (91 U/L) | 98 | 91 | 80 |
| base) | 1/1 | 100 | (183 U/L) | 98 | 92 | 81 |
| PGAM-M | 1/8 | 100 | (332 U/L) | 0 | 0 | 0 |
| standard | 1/4 | 100 | (676 U/L) | 0 | 0 | 0 |
| (pooled serum | 1/2 | 100 | (1365 U/L) | 0 | 0 | 0 |
| base) | 1/1 | 100 | (2727 U/L) | 0 | 0 | 0 |

Unit: %

EXAMPLE 2

PGAM activity in a serum sample derived from a patient with cerebral apoplexy (within two hours, 6 to 12 hours and 1 to 3 days after the attack) was measured using potassium tetrathionate as the M-type PGAM isozyme inhibitor in accordance with the procedure and conditions as shown in Table 3 below.

TABLE 3

Procedure and Conditions for Determination of Activity

1. Preparation of a serum sample
   Collection of blood (blood from vein, about 2 ml)
   ↓ Standing for 30 min
   ↓ Centrifugation (3000 rpm, 8 min)
   Supernatant (serum sample, about 1 ml)
2. Determination of PGAM activity
   Determined using Hitachi 7150 model automatic analyzer

| Serum | 5 μl |
|---|---|
| Reagent 1 (R1) | 250 μl |
| Reagent 2 (R2) | 41 μl |

These are added in this order and the decrease of NADH (refer to the principle of the assay) is measured by the rate assay.

Measuring temperature: 37° C.

Main wavelength: 340 nm, Secondary wavelength: 405 nm

As the assay reagent, Reagent 1 (R-1), potassium tetrathionate and Reagent 2 (R-2) having the following compositions were used.

(Reagent 1): R-1

|  |  | (ml) |
|---|---|---|
| TEA buffer | (0.1 mol/l, pH 7.6) | 40.32 |
| MgSO$_4$ | (0.1 mol/l) | 0.54 |
| NADH | (14 mmol/l) | 0.90 |
| ADP | (21 mmol/l) | 1.80 |
| G-2,3-P2 | (7 mmol/l) | 0.90 |
| LDH | (5 mg protein/ml) | 0.18 |
| PK | (2 mg protein/ml) | 0.18 |
| Enolase | (10 mg protein/ml) | 0.18 |
|  |  | (Total: 45.00 ml) |

Potassium tetrathionate (molecular weight of 302.4) was added to and dissolved in the PGAM activity assay reagent (R-1) so as to give a concentration of 2.25 mM (final concentration of 1.9 mM) (15 mg of potassium tetrathionate was dissolved in 22 ml of the R-1 reagent) and the M-type isozyme was inactivated to prepare a B-type PGAM activity assay reagent.

(Reagent 2): R-2

|  |  | (ml) |
|---|---|---|
| G-3-P | (95 mmol/l) | 3.00 |
| TEA buffer | (0.1 mol/l, pH 7.6) | 5.20 |
|  |  | (Total: 8.20 ml) |

Five µl of a serum sample was combined with 250 µl of the solution of Reagent 1 (R-1) in which potassium tetrathionate was dissolved, and the mixture was allowed to stand for 5 minutes. During this period, the M-type (and MB-type) PGAM was inactivated and inhibited, and then the B-type PGAM activity was determined using Reagent 2 (R-2).

The reaction was initiated (substrate start) by adding 41 µl of Reagent 2 (R-2) because it contained glycerate-3-phosphate (substrate). The assay was started about 1.5 minutes after the addition of Reagent 2.

The assay was carried out using Hitachi 7150 model automatic analyzer with setting the assay code to RATE-A: 32-39 and the measuring temperature to 37° C. The decrease in absorbance A 340 nm associated with the decrease of NADH was measured for about 1.5 minutes. It should be noted that the assay was carried out at the secondary wavelength of 405 nm.

One unit of the enzyme (1 U: 1 unit) was defined as the amount of the enzyme that reduces 1 µmol of NADH for 1 minute at 37° C. Actual measured values were calculated by multiplying the rate assay value by a calibrating factor (K FACTOR). The results thus obtained are shown in FIG. 1.

As clearly shown in the results, B-PGAM activity is specifically high within two hours after the onset of cerebral apoplexy, and it has been proved that B-PGAM is a marker suitable for cerebral apoplexy.

EXAMPLE 3

PGAM in the above three serum samples were assayed in the same manner as in the above Example using only Reagent 1 and Reagent 2 exclusive of potassium tetrathionate (no use of the inhibitor means the total PGAM assay). As a result, the same tendency as in the case of the B-PGAM assay was obtained, and it has been proved that T-PGAM is an excellent marker for cerebral apoplexy as well as B-PGAM.

Effect of the Invention

According to the present invention, the B-type isozyme can be determined rapidly and accurately by, in particular, using the PGAM inhibitor. Further, PGAM-B has been proved to be a suitable marker for cerebral apoplexy. The assay method of the present invention enables rapid and accurate diagnosis of cerebral apoplexy. Moreover, it can be found that T-PGAM is also useful as a novel marker for cerebral apoplexy, although it is somewhat inferior in accuracy to the case of PGAM-B.

We claim:

1. A method for assaying phosphoglyceric acid mutase (PGAM) in a blood or blood serum sample, comprising the steps of:

(1) mixing the blood or blood serum sample with an assay reagent 1 containing 2,3-bisphosphoglycerate (glycerate-2,3-P2), enolase, ADP, pyruvate kinase (PK), NADH and lactate dehydrogenase (LDH);

(2) mixing the mixture obtained in step (1) with an assay reagent 2 containing 3-phosphoglycerate (glycerate-3-P), whereby:

(a) the glycerate-3-P is converted to 2-phosphoglycerate (glycerate-2-P) in the presence of PGAM in the blood serum sample and glycerate-2,3-P2;

(b) the glycerate-2-P is converted to PEP and H$_2$O in the presence of the enolase;

(c) the PEP is reacted with the ADP in the presence of the PK to give pyruvate and ATP; and (d) the pyruvate is reacted with the NADH in the presence of the LDH to give lactate and NAD; and (3) conducting the rate assay of the decrease of the NADH in (d) of step (2), thereby determining a total PGAM activity.

2. The method according to claim 1, wherein the blood serum is derived from a patient with cerebral apoplexy.

3. A method for assaying phosphoglyceric acid mutase (PGAM) in a blood or blood serum sample, comprising the steps of:

(1) mixing the blood or blood serum sample with an assay reagent containing 2,3-bisphosphoglycerate (glycerate-2,3-P2), enolase, ADP, pyruvate kinase (PK), NADH, lactate dehydrogenase (LDH) and 3-phosphoglycerate (glycerate-3-P), whereby:

(a) the glycerate-3-P is converted to 2-phosphoglycerate (glycerate-2-P) in the presence of PGAM in the serum sample and glycerate-2,3-P2;

(b) the glycerate-2-P is converted to PEP and H$_2$O in the presence of enolase;

(c) the PEP is reacted with ADP in the presence of the PK to give pyruvate and ATP; and (d) the pyruvate is reacted with NADH in the presence of the LDH to give lactate and NAD; and (2) conducting the rate assay of the decrease of the NADH in (d) of step (1), thereby determining a total PGAM activity.

4. The method according to claim 3, wherein the blood serum sample is derived from a patient with cerebral apoplexy.

5. A method for assaying phosphoglyceric acid mutase (PGAM) in a blood or blood serum sample, comprising the steps of:

(1) mixing a PGAM inhibiting substance capable of inhibiting the activity of a PGAM isozyme comprising a M-type subunit with an assay reagent 1 containing 2,3-bisphosphoglycerate (glycerate-2,3-P2), enolase, ADP, pyruvate kinase (PK), NADH and lactate dehydrogenase (LDH);

(2) mixing the mixture obtained in step (1) with the blood or blood serum sample, thereby inhibiting said activity in the blood or blood serum sample;

(3) mixing the resulting mixture with an assay reagent 2 containing 3-phosphoglycerate (glycerate-3-P), whereby:

(a) the glycerate-3-P is converted to 2-phosphoglycerate (glycerate-2-P) in the presence of PGAM in the serum sample and glycerate-2,3-P2;

(b) the glycerate-2-P is converted to PEP and $H_2O$ in the presence of enolase;

(c) the PEP is reacted with the ADP in the presence of the PK to give pyruvate and ATP; and (d) the pyruvate is reacted with the NADH in the presence of the LDH to give lactate and NAD; and (4) conducting the rate assay of the decrease of the NADH in (d) of step (3), thereby determining the resulting residual PGAM activity.

6. The method according to claim 5, wherein the substance capable of inhibiting the activity of a PGAM isozyme comprising a M-type subunit is a substance capable of inhibiting PGAM-M activity.

7. The method according to claim 6, wherein the substance capable of inhibiting PGAM-M activity is potassium tetrathionate.

8. The method according to claim 5, wherein the blood serum is derived from a patient with cerebral apoplexy.

9. A method for assaying phosphoglyceric acid mutase (PGAM) in a blood or blood serum sample, comprising the steps of:

(1) mixing the blood or blood serum sample with an assay reagent 1 containing a PGAM inhibiting substance capable of inhibiting a PGAM isozyme comprising a M-type subunit, 2,3-bisphosphoglycerate (glycerate-2,3-P2), enolase, ADP, pyruvate kinase (PK), NADH and lactate dehydrogenase (LDH), thereby inhibiting said activity in the blood or blood serum sample;

(2) mixing the resulting mixture in step (1) with as assay reagent 2 containing 3-phosphoglycerate (glycerate-3-P), whereby:

(a) the glycerate-3-P is converted to 2-phosphoglycerate (glycerate-2-P) in the presence of PGAM in the serum sample and glycerate-2,3-P2;

(b) the glycerate-2-P is converted to PEP and $H_2O$ in the presence of enolase;

(c) the PEP is reacted with the ADP in the presence of the PK to give pyruvate and ATP; and (d) the pyruvate is reacted with the NADH in the presence of the LDH to give lactate and NAD; and (3) conducting the rate assay of the decrease of the NADH in (d) of step (2), thereby determining the resulting residual PGAM activity.

10. The method according to claim 9, wherein the PGAM inhibiting substance capable of inhibiting the activity of a PGAM isozyme comprising a M-type subunit is a substance capable of inhibiting PGAM-M activity.

11. The method according to claim 10, wherein the substance capable of inhibiting PGAM-M activity is potassium tetrathionate.

12. The method according to claim 9, wherein the blood serum sample is derived from a patient with cerebral apoplexy.

13. An assay reagent for assaying a total phosphoglyceric acid mutase (PGAM), which contains 2,3-bisphosphoglycerate (glycerate-2,3-P2), enolase, ADP, pyruvate kinase (PK), NADH, lactate dehydrogenase (LDH) and 3-phosphoglycerate (glycerate-3-P).

14. An assay reagent set for assaying a total phosphoglyceric acid mutase (PGAM), comprising an assay reagent 1 containing 2,3-bisphosphoglycerate (glycerate-2,3-P2), enolase, ADP, pyruvate kinase (PK), NADH and lactate dehydrogenase (LDH), and an assay reagent 2 containing 3-phosphoglycerate (glycerate-3-P).

15. An assay reagent set for inhibiting the activity of a phospoglyceric acid mutase (PGAM) isozyme comprising a M-type subunit and assaying the resulting residual PGAM activity, comprising an assay reagent 1 containing a PGAM inhibiting substance capable of inhibiting the activity of a PGAM isozyme comprising a M-type subunit, 2,3-bisphosphoglycerate (glycerate-2,3-P2), enolase, ADP, pyruvate kinase (PK), NADH and lactate dehydrogenase (LDH), and an assay reagent 2 containing 3-phosphoglycerate (glycerate-3-P).

16. The assay reagent set according to claim 15, wherein the substance capable of inhibiting the activity of a PGAM isozyme comprising a M-type subunit is a substance capable of inhibiting PGAM-M activity.

17. The assay reagent set according to claim 16, wherein the substance capable of inhibiting PGAM-M activity is potassium tetrathionate.

* * * * *